(12) United States Patent
Boon et al.

(10) Patent No.: US 6,488,932 B1
(45) Date of Patent: *Dec. 3, 2002

(54) METHOD FOR TREATING CANCER BY ADMINISTERING MAGE-DERIVED PEPTIDES

(75) Inventors: Thierry Boon; Pierre van der Bruggen; Etienne De Plaen; Christophe Lurquin, all of Brussels (BE); Catia Traversari, Milan (IT)

(73) Assignee: Ludwig Institute for Cancer Research, New York, NY (US)

( * ) Notice: Subject to any disclaimer, the term of this patent is extended or adjusted under 35 U.S.C. 154(b) by 302 days.

This patent is subject to a terminal disclaimer.

(21) Appl. No.: 08/571,263

(22) Filed: Dec. 12, 1995

Related U.S. Application Data

(62) Division of application No. 08/354,679, filed on Dec. 13, 1994, which is a division of application No. 07/938,334, filed on Aug. 31, 1992, now Pat. No. 5,405,940.

(51) Int. Cl.[7] ................ C07K 5/00; A61K 39/395; A61K 39/00
(52) U.S. Cl. ................ 424/185.1; 424/277.1; 424/193.1; 530/328; 530/320; 530/335; 530/402
(58) Field of Search .......... 424/185.1, 277.1, 424/193.1; 530/328, 300, 335, 402

(56) References Cited

U.S. PATENT DOCUMENTS

| 5,342,774 A | 8/1994 | Boon et al. ............. 435/240.2 |
| 5,405,940 A | 4/1995 | Boon et al. ............. 530/328 |
| 5,462,871 A | 10/1995 | Boon et al. ............. 435/240.2 |

FOREIGN PATENT DOCUMENTS

| WO | WO9202543 | 2/1992 |
| WO | WO9220356 | 11/1992 |
| WO | WO9403205 | 2/1994 |

OTHER PUBLICATIONS

Rothbard, J.B., Curr. Opin. Immunol. 2:99–105, Major histocompatibility complex–peptide interactions, 1989.*
Engelhard, V. H., Curr. Opin. Immunol. 6:13–23, Structure of peptides associated with MHC Class I molecules, 1994.*
Ochoa–Garay, J. et al., Mol. Immunol. 34(3):273–281, The ability of peptides to induce cytotoxic T cells in vitro does not strongly correlate with their affinity for the H–2L–d molecule: implications ofr vaccine design and immunotherapy, 1997.*

Parham, P et al., Immunol. Rev. 143:142–180, The origins of HLA–A, B, C polymorphism, 1995.*

Parker, K. C. et al., J. Immunol. 149:3580–3587, Sequence motifs important for peptide binding to the human MHC Class I molecule, HLA–A2, Dec. 1, 1992.*

Salgaller, M. L. et al., Cancer Immunol. Immunother. 39:105–116, Generation of specific anti–melanoma reactivity by stimulation of human tumor–infiltrating lymphocytes with MAGE–1 synthetic peptide, 1994.*

Smilek, D. et al., PNAS 88:9633–9637, A single amino acid change in a myelin basic protein peptide confers the capacity to prevent rather than induce experimental autoimmune encephalomyelitis, Nov. 1991.*

Van der Zee, R. et al., Eur. J. Immunol. 19:43–47, Efficient mapping and characterization of a T cell epitope by the simultaneous synthesis of multiple peptides, 1989.*

Rötzschke et al., "Isolated and analysis of naturally processed Viral peptides as recognized by cytolytic T cells", Nature 348:252–254 (1990).

Van der Bruggen et al., "A Gene Encoding An Antigen Recognized By Cytolytic T Lymphocytes on a Human Melanoma", Science 254:1643–1647 (Dec. 1991).

Traversari et al., "A Nonapeptide Encoded by Human Gene MAGE–1 Is Recognized on HLA–A1 By Cytolytic T Lymphocytes Directed Against Tumor Antigen MZ2–E". J.Exp.Med. 176: 1453–1457 (1992).

* cited by examiner

Primary Examiner—Christina Y. Chan
Assistant Examiner—Martha Lubet
(74) Attorney, Agent, or Firm—Fulbright & Jaworski, LLP

(57) ABSTRACT

The invention involves the reception of particular nonapeptides by HLA molecules. The nonapeptides are derived from expression products of the MAGE gene family. The resulting complexes are identified by cytolytic T cells. Such recognition may be used in diagnostics, or therapeutically.

4 Claims, 4 Drawing Sheets

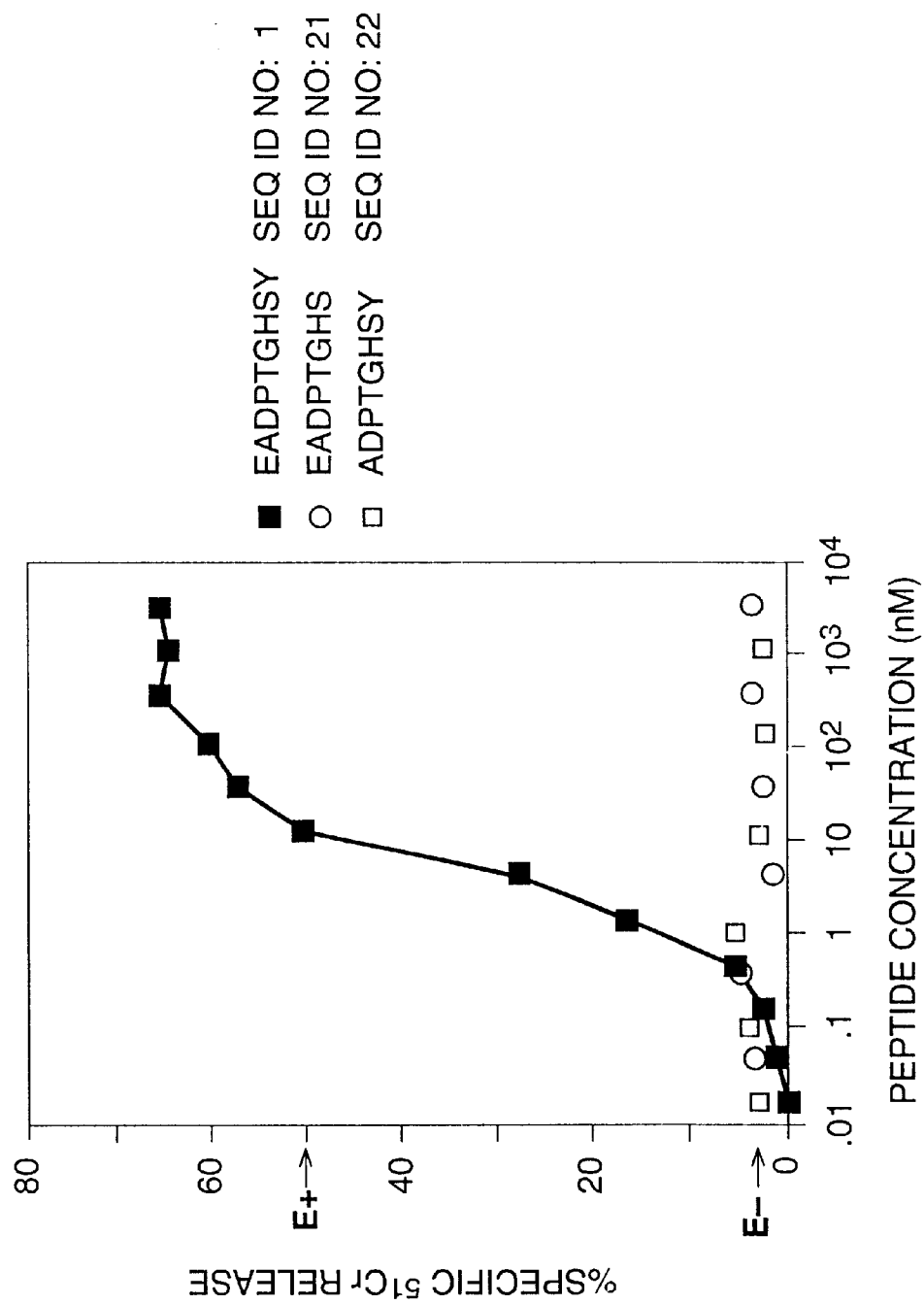

FIG. 4

| MAGE 1  | E | A | D | P | T | G | H | S | Y |
| MAGE 2  | E | V | V | P | I | S | H | L | Y |
| MAGE 21 | E | V | V | R | I | G | H | L | Y |
| MAGE 3  | E | V | D | P | I | G | H | L | Y |
| MAGE 4  | E | V | D | P | A | S | N | T | Y |
| MAGE 41 | E | V | D | P | T | S | N | T | Y |
| MAGE 5  | E | A | D | P | T | S | N | T | Y |
| MAGE 51 | E | A | D | P | T | S | N | T | Y |
| MAGE 6  | E | V | D | P | I | G | H | V | Y |

| MAGE 1  | GAA | GCA | GAC | CCC | ACC | GGC | CAC | TCC | TAT |
| MAGE 2  | GAA | GTG | GTC | CCC | ATC | AGC | CAC | TTG | TAC |
| MAGE 21 | GAA | GTG | GTC | CGC | ATC | GGC | CAC | TTG | TAC |
| MAGE 3  | GAA | GTG | GAC | CCC | ATC | GGC | CAC | TTG | TAC |
| MAGE 4  | GAA | GTG | GAC | CCC | GCC | AGC | AAC | ACC | TAC |
| MAGE 41 | GAA | GTG | GAC | CCC | ACC | AGC | AAC | ACC | TAC |
| MAGE 5  | GAA | GCG | GAC | CCC | ACC | AGC | AAC | ACC | TAC |
| MAGE 51 | GAA | GCG | GAC | CCC | ACC | AGC | AAC | ACC | TAC |
| MAGE 6  | GAA | GTG | GAC | CCC | ATC | GGC | CAC | GTG | TAC |

```
                        SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE: genomic DNA (ix) FEATURE:
        (A) NAME/KEY:  MAGE-1 nonapeptide coding sequence (xi) SEQUENCE DESCRIPTION:  SEQ ID NO: 1:

GAAGCAGACC CCACCGGCCA CTCCTAT                                        27

(2) INFORMATION FOR SEQ ID NO: 2:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE: genomic DNA (ix) FEATURE:
        (A) NAME/KEY:  MAGE-2 nonapeptide coding sequence (xi) SEQUENCE DESCRIPTION:  SEQ ID NO: 2:

GAAGTGGTCC CCATCAGCCA CTTGTAC                                        27

(2) INFORMATION FOR SEQ ID NO: 3:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear
```

(ii) MOLECULE TYPE: genomic DNA (ix) FEATURE:
            (A) NAME/KEY:  MAGE-21 nonapeptide coding sequence (xi) SEQUENCE DESCRIPTION:  SEQ ID NO: 3:

GAAGTGGTCC GCATCGGCCA CTTGTAG                                              27

(2) INFORMATION FOR SEQ ID NO: 4:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (ii) MOLECULE TYPE: genomic DNA (ix) FEATURE:
            (A) NAME/KEY:  MAGE-3 nonapeptide coding sequence (xi) SEQUENCE DESCRIPTION:  SEQ ID NO: 4:

GAAGTGGACC CCATCGGCCA CTTGTAC                                              27

(2) INFORMATION FOR SEQ ID NO: 5:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (ii) MOLECULE TYPE: genomic DNA (ix) FEATURE:
            (A) NAME/KEY:  MAGE-4 nonapeptide coding sequence (xi) SEQUENCE DESCRIPTION:  SEQ ID NO: 5:

GAAGTGGACC CCGCCAGCAA CACCTAC                                              27

(2) INFORMATION FOR SEQ ID NO: 6:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (ii) MOLECULE TYPE: genomic DNA (ix) FEATURE:
            (A) NAME/KEY:  MAGE-41 nonapeptide coding sequence (xi) SEQUENCE DESCRIPTION:  SEQ ID NO: 6:

GAAGTGGACC CCACCAGCAA CACCTAC                                              27

(2) INFORMATION FOR SEQ ID NO: 7:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (ii) MOLECULE TYPE: genomic DNA (ix) FEATURE:
            (A) NAME/KEY:  MAGE-5 nonapeptide coding sequence (xi) SEQUENCE DESCRIPTION:  SEQ ID NO: 7:

GAAGCGGACC CCACCAGCAA CAACTAC                           27

(2) INFORMATION FOR SEQ ID NO: 8:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE: genomic DNA (ix) FEATURE:
        (A) NAME/KEY:  MAGE-51 nonapeptide coding sequence (xi) SEQUENCE DESCRIPTION:  SEQ ID NO: 8:

GAAGCGGACC CCACCAGCAA CACCTAC                           27

(2) INFORMATION FOR SEQ ID NO: 9:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE: genomic DNA (ix) FEATURE:
        (A) NAME/KEY:  MAGE-6 nonapeptide coding sequence (xi) SEQUENCE DESCRIPTION:  SEQ ID NO: 9:

GAAGTGGACC CCATCGGCCA CGTGTAC                           27

(2) INFORMATION FOR SEQ ID NO: 10:

(i) SEQUENCE CHARACTERISTICS:
        (A) LENGTH:  19 base pairs
        (B) TYPE:  nucleic acid
        (C) STRANDEDNESS:  single
        (D) TOPOLOGY:  linear (ii) MOLECULE TYPE: DNA (xi) SEQUENCE DESCRIPTION:  SEQ ID NO: 10:

CAGGGAGCCA GTCACAAAG                                    19

(2) INFORMATION FOR SEQ ID NO: 11:

(i) SEQUENCE CHARACTERISTICS:
        (A) LENGTH:  20 base pairs
        (B) TYPE:  nucleic acid
        (C) STRANDEDNESS:  single
        (D) TOPOLOGY:  linear (ii) MOLECULE TYPE: DNA (xi) SEQUENCE DESCRIPTION:  SEQ ID NO: 11:

ACTCAGCTCC TCCCAGATTT                                   20

(2) INFORMATION FOR SEQ ID NO: 12:

(i) SEQUENCE CHARACTERISTICS:
        (A) LENGTH:  9 amino acids
        (B) TYPE:  amino acid
        (C) STRANDEDNESS:  single
        (D) TOPOLOGY:  linear (ii) MOLECULE TYPE: protein (xi) SEQUENCE DESCRIPTION: SEQ ID NO: 12:

Glu Ala Asp Pro Thr Gly His Ser Tyr
                5

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Glu Ala Asp Pro Thr Gly His Ser
                5

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Ala Asp Pro Thr Gly His Ser Tyr
                5

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Glu Val Val Pro Ile Ser His Leu Tyr
                5

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Glu Val Val Arg Ile Gly His Leu Tyr
                5

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

Glu Val Asp Pro Ile Gly His Leu Tyr
                5

(2) INFORMATION FOR SEQ ID NO: 18:

(i) SEQUENCE CHARACTERISTICS:
        (A) LENGTH: 9 amino acids
        (B) TYPE:  amino acid
        (C) STRANDEDNESS: single
        (D) TOPOLOGY:  linear (ii) MOLECULE TYPE: protein (xi) SEQUENCE DESCRIPTION: SEQ ID NO: 18:

Glu Val Asp Pro Ala Ser Asn Thr Tyr
                5

(2) INFORMATION FOR SEQ ID NO: 19:

(i) SEQUENCE CHARACTERISTICS:
        (A) LENGTH: 9 amino acids
        (B) TYPE:  amino acid
        (C) STRANDEDNESS: single
        (D) TOPOLOGY:  linear (ii) MOLECULE TYPE: protein (xi) SEQUENCE DESCRIPTION: SEQ ID NO: 19:

Glu Val Asp Pro Thr Ser Asn Thr Tyr
                5

(2) INFORMATION FOR SEQ ID NO: 20:

(i) SEQUENCE CHARACTERISTICS:
        (A) LENGTH: 9 amino acids
        (B) TYPE:  amino acid
        (C) STRANDEDNESS: single
        (D) TOPOLOGY:  linear (ii) MOLECULE TYPE: protein (xi) SEQUENCE DESCRIPTION: SEQ ID NO: 20:

Glu Ala Asp Pro Thr Ser Asn Thr Tyr
                5

(2) INFORMATION FOR SEQ ID NO: 21:

(i) SEQUENCE CHARACTERISTICS:
        (A) LENGTH: 9 amino acids
        (B) TYPE:  amino acid
        (C) STRANDEDNESS: single
        (D) TOPOLOGY:  linear (ii) MOLECULE TYPE: protein (xi) SEQUENCE DESCRIPTION: SEQ ID NO: 21:

Glu Ala Asp Pro Thr Ser Asn Thr Tyr
                5

(2) INFORMATION FOR SEQ ID NO: 22:

(i) SEQUENCE CHARACTERISTICS:
        (A) LENGTH: 9 amino acids
        (B) TYPE:  amino acid
        (C) STRANDEDNESS: single
        (D) TOPOLOGY:  linear

```
        (ii) MOLECULE TYPE: protein (xi) SEQUENCE DESCRIPTION: SEQ ID NO: 22:

Glu Val Asp Pro Ile Gly His Val Tyr
                5

(2) INFORMATION FOR SEQ ID NO: 23:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: protein (ix) FEATURE:
             (D) OTHER INFORMATION: Xaa3 is Pro or Arg and Xaa1, Xaa2,
                 Xaa4-Xaa7 may be any amino acid.

(xi) SEQUENCE DESCRIPTION: SEQ ID NO: 23:

Glu Xaa Xaa Xaa Xaa Xaa Xaa Xaa Tyr
                5

(2) INFORMATION FOR SEQ ID NO: 24:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: protein (ix) FEATURE:
             (D) OTHER INFORMATION: Xaa4 is Thr, Ile or Ala and Xaa1,
                 Xaa4 and Xaa6-Xaa7 may be any amino acid.

(xi) SEQUENCE DESCRIPTION: SEQ ID NO: 24:

Glu Xaa Xaa Xaa Xaa Xaa Xaa Xaa Tyr
                5

(2) INFORMATION FOR SEQ ID NO: 25:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: protein (ix) FEATURE:
             (D) OTHER INFORMATION: Xaa6 is His or Asn and Xaa1-Xaa5 and
                 Xaa7 may be any amino acid.

(xi) SEQUENCE DESCRIPTION: SEQ ID NO: 25:

Glu Xaa Xaa Xaa Xaa Xaa Xaa Xaa Tyr
```

METHOD FOR TREATING CANCER BY ADMINISTERING MAGE-DERIVED PEPTIDES

RELATED APPLICATIONS

This application is a divisional of Ser. No. 08/354,679, filed on Dec. 13, 1994, and pending, which is a divisional of Ser. No. 07/938,334, filed on Aug, 31, 1992, now U.S. Pat. No. 5,405,940.

FIELD OF THE INVENTION

This invention relates to immunogenetics and to peptide chemistry. More particularly, it relates to a class of nonapeptides useful in various ways, such as immunogens and as materials which target and bind MHC/HLA molecules, as well as a cellular model useful in the testing of peptides and other molecules as vaccines, especially cancer vaccines. Most particularly, it relates to the so-called "tumor rejection antigens", in particular the MAGE family of these antigens.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺ "cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980), Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and a class of antigens, referred to as "tum-" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and sibille et al., J. Exp. Med. 172: 35–45 (1990), the discloures of which are incorporated by reference. The P815 tumor is a mastocytoma, induced in a DBA/2 mouse with methylcholanthrene and cultured as both an in vitro tumor and a cell line. The P815 Line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce tum− variants. Since the tum− phenotype differs from that of the parent cell line, one expects a difference in the DNA of tum− cell lines as compared to their tum+ parental lines, and this difference can be exploited to locate the gene of interest in tum− cells. As a result, it was found that genes of tum− variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum− antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that a particular nonapeptide is in fact presented on the surface of tumor cells, and that the presentation of the nonapeptide requires that the presenting molecule be HLA-A1. Complexes of the MAGE-1 tumor rejection antigen (the "TRA" or nonapeptide") leads to lysis of the cell presenting it by cytolytic T cells ("CTLs"). This observation has both diagnostic and therapeutic implications, as discussed herein.

It has also been found that, when comparing homologous regions of various MAGE genes to the region of the MAGE-1 gene coding for the relevant nonapeptide, there is a great deal of homology. Indeed, these observations lead to one of the aspects of the invention, which is a family of nonapeptides all of which have the same N-terminal and C-terminal amino acids. These nonapeptides can be used for various purposes which includes their use as immunogens, either alone or coupled to carrier peptides. Nonapeptides are of sufficient size to constitute an antigenic epitope, and the antibodies generated thereto may then be used to identify the nonapeptide, either as it exists alone, or as part of a larger polypeptide.

The nonapeptides may also be used as agents to identify various HLA subtypes on the surface of tumor cells, such as melanomas. Via this ability they may serve either as diagnostic markers, or as therapeutic agents. These features are discussed infra.

Also considered part of the invention are the nucleic acid sequences which code for the nonapeptides. These nucleic acid sequences may serve as diagnostic probes for tumor presence.

It has also been found that a cellular model can now be used, wherein a non-human cell can be transfected with a nucleic acid sequence coding for a human HLA molecule. The resulting transfectant can then be used to test for nonapeptide specificity of the particular HLA molecule, or as the object of a second transfection with a MAGE gene. The co-transfectant can then be used to determine whether the particular MAGE based TRA is presented by the particular HLA molecule. These, and other features of the invention, are set forth in the description which follows.

BRIEF DESCRIPTION OF THE FIGURES

FIG. 2 shows lytic studies in which cells were incubated with various MAGE 1 peptides.

FIG. 3 compares lysis of mouse cells transfected with HLA-A1 genes, in the presence of the MAGE-1 nonapeptide, and when cotransfected with the sequence coding for MAGE-1.

FIG. 4 compares nonapeptides from various homologous sections of MAGE genes and the nucleic acid sequences coding for these nonapeptide. SEQ ID NOS: 1–9 show homologous nonapeptides from MAGE genes and the nucleic acid sequences coding for these.

DETAILED DESCRIPTION OF PREFERRED EMBODIMENTS

EXAMPLE 1

Figure 1:
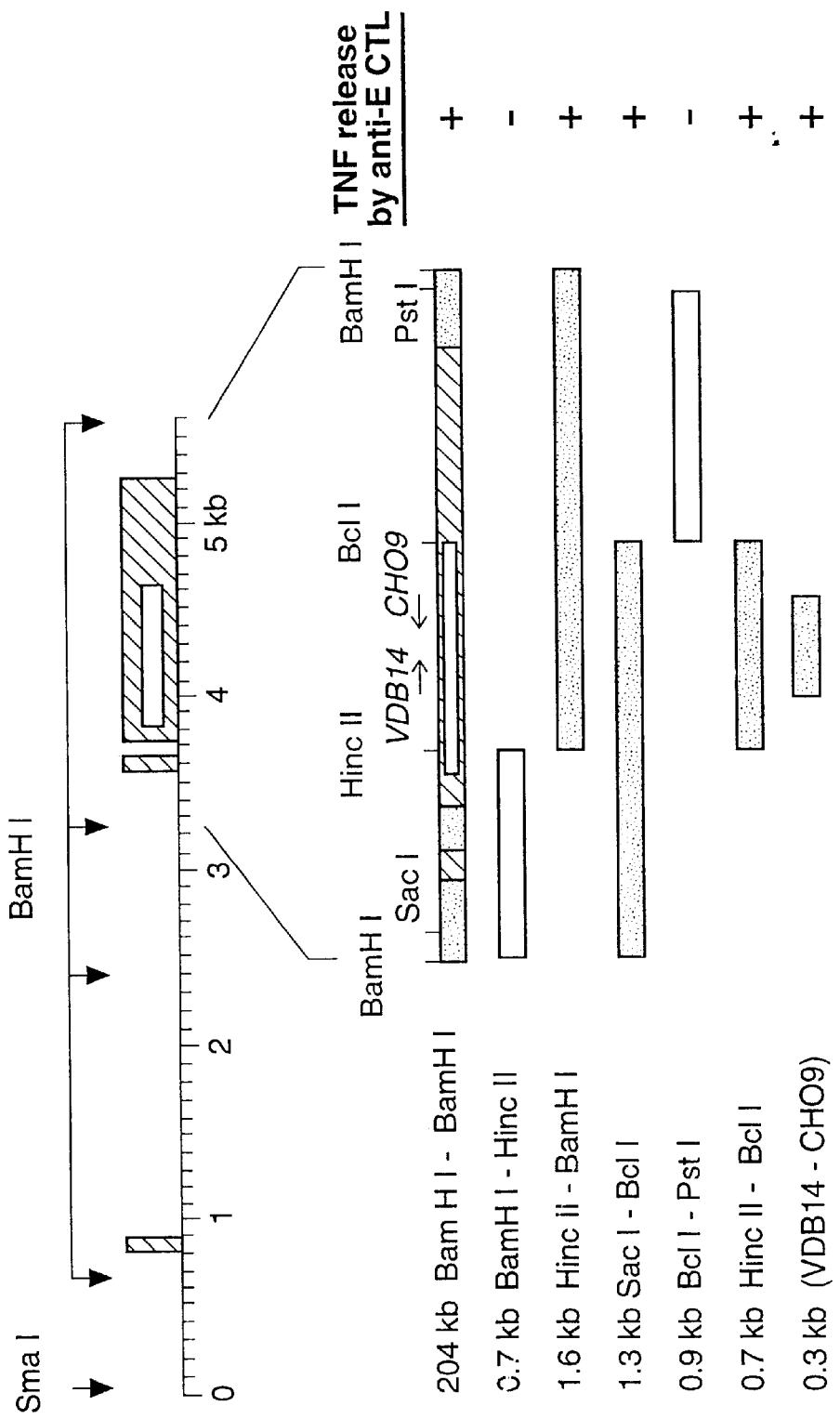
FIG. 1 outlines the procedure by which a 300 base pair fragment of MAGE-1 gene was identified as coding for the relevant tumor rejection antigen.

The 2.4 Kb BamIII fragment, described by van der Bruggen et al., Science 254: 1643 (1991), the disclosure of which is incorporated by reference, is known to contain only exons 2 and 3 of the gene coding for MAGE-1 protein. The fragment transfers expression of antigen MZ2-E to E− antigen loss cell line variant MZ2-MEL.2.2. and leads to lysis of the transfectants by E+ CTLs. Previous work by DePlaen et al., Proc. Natl. Acad. Sci. USA 85: 2274 (1988), and Chomez et al., Immunogenetics 35: 241 (1990), had established that small gene fragments containing antigen peptide coding sequences regularly express those antigens, even when not transfected in the form of expression vectors. In view of these observations, experiments were carried out with smaller fragments of the 2.4 kb fragment. Various restriction enzymes were used to cut the 2.4 kb fragment into smaller fragments. The resulting, smaller fragments were cloned into plasmid vector pTZ18R. A 300 base pair fragment taken from exon 3 was obtained via polymerase chain reaction ("PCR") amplification, using oligonucleotides VDB 14 (SEQ ID NO: 10):

5'-CAGGGAGCCAGTCACAAAG-3' (SEQ ID NO:10) and CHO 9 (SEQ ID NO: 11):

5'-ACTCAGCTCCTCCCAGATTT-3' (SEQ ID NO: 12).

These primers amplify a 300 base pair fragment of MAGE 1. between positions 422 and 722 of exon 1. The fragment was cloned into expression vector PSVK3. The new constructs were cotransfected with plasmid pSVtkneoβ into the MZ2.MEL 2.2 cell lines. This was accomplished using the calcium phosphate precipitation method (Traversari et al., Immunogenetics 35: 145 (1992); Wölfel et al., Immunogenetics 26: 178 (1987)), using 4×10$^6$ cells and 3 ug of pSVtneoβ (Nicolas et al., CSH Conf. Cell Prolif 10: 469 (1983), and 30 ug of the ptZ18R or PSVK3 constructs. The transfectants were then selected in medium containing neomycin analog G418. Fifteen days after transfection, resistant cells were tested for their ability to stimulate TNF production by the anti-E antigen specific CTL 82/30. This was accomplished by adding 100 ul samples, containing 1500 cell of CTL 82/30 to $4 \times 10^4$ transfected cells. Supernatant samples (50 ul) were harvested and added to $3 \times 10^4$ WEHI 164 clone 13 cells (Espevik et al., J. Immunol. Meth. 95: 99 (1986)), to evaluate TNF presence. Mortality of WEHI cells was estimated 24 hours later, using an MTT colorimetric assay as per, e.g., Traversari et al., supra.

As shown in FIG. 1, these experiments identified a 300 base pair fragment from MAGE-1 exon 3 capable of efficient transferring of expression of antigen MZ2E.

EXAMPLE 2

The MAGE-1 gene belongs to a family of several highly related genes as per van der Bruggen et al., supra. Prior experiments had noted that MAGE-2 and MAGE-3 did not direct expression of antigen MZ2-E. As the 300 base pair fragment clearly did, the homologous sections of MAGE-2 and MAGE-3 genes were compared to the 300 base pair fragment. Differences were clear, and several 15 amino acid peptides were synthesized, using F-moc for transient N-terminal protection, in accordance with Atherton et al., J. Chem. Soc. 1: 538 (1981). The peptides were purified by C-18 reverse phase HPL,C, and characterized by amino acid analysis.

Once the peptides were secured, they were tested in lysis assays, using the chromium release methodology of Boon et al., J. Exp. Med. 152: 1184 (1980). Briefly, 1000 $^{51}$Cr labeled E⁻ target cells were incubated in 96 well microplates, using various concentrations of peptides for 30 minutes at 37° C.

An equal volume of CTL containing sample was added (cell line 82/30), the number of CTLs being five times that of their target. Chromium release was measured after four hours. Sensitization of E⁻ cells to lysis by the anti E CTLs was observed with a peptide that corresponds to codons 158–172 of the large open reading frame of MAGE-1. Shorter peptides were prepared and efficient lysis was observed with peptide: Glu Ala Asp Pro Thr Gly His Ser Tyr (SEQ ID NO: 12).

The results, shown in FIG. 2, demonstrate that the first and ninth amino acids were critical for binding and effecting lysis. This is in accordance with prior reports stating that MHC-I molecules generally are bound by nonapeptides (Rotzschke et al., Nature 348: 252 (1990)). FIG. 2 also shows that half maximum lysis was obtained at a peptide concentration of 5 nM.

EXAMPLE 3

Experiments were carried out to determine what molecule presented the relevant MAGE-1 antigen. To accomplish this, an HLA-A1 gene, as taught by Girdlestone, Nucl. Acids. Res. 18: 6701 (1990), was transfected into a mouse cell line, P1.HTR. This line is a highly transfectable variant of mouse mastocytoma cell line P815. The resulting transfectants, referred to as "P1.HTR.A1", were incubated in the presence of the nonapeptide discussed supra, using the same lysis assay. Controls were also used.

Figure 3A:
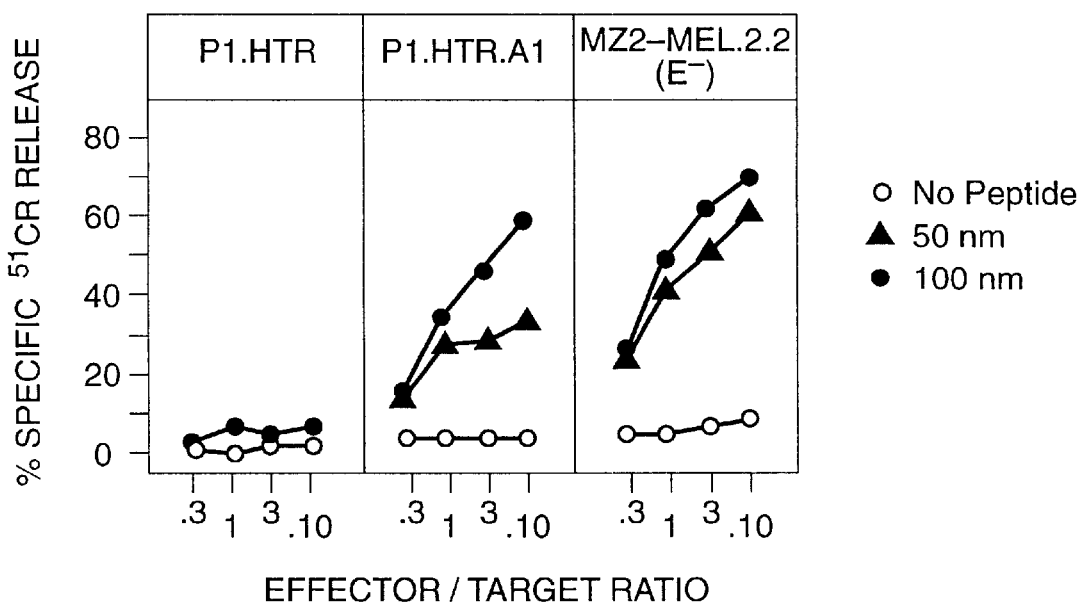
In FIG. 3A, the cell lines P1.HTR, P1.HTR.A1 and MZ2-MEL.2.2 are tested; with no peptide, and at concentrations of 50 nm and 100 nm of peptide.
Figure 3B:
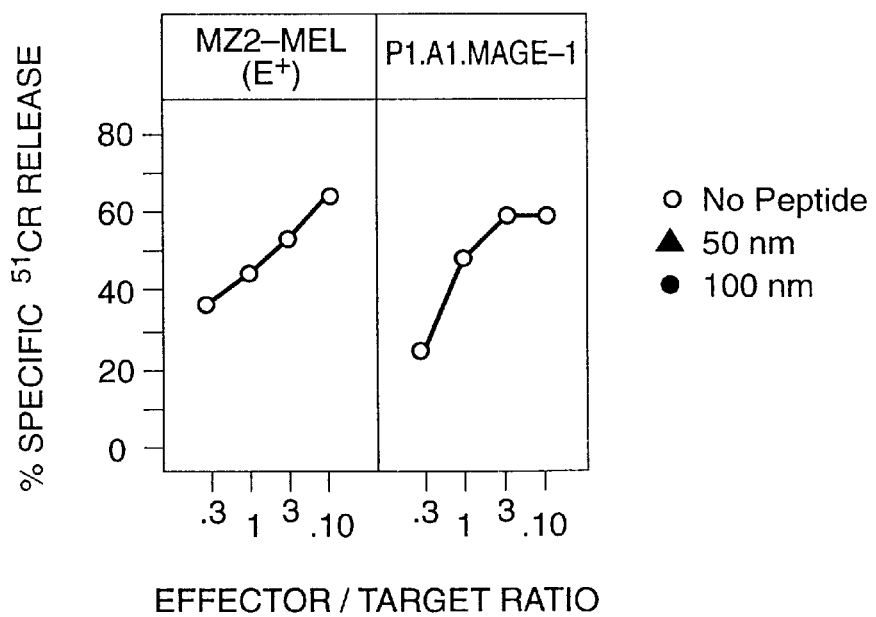
In FIG. 3B, cell lines MZ2-MEL and P1.A1 MAGE-1 were tested with no peptide.

FIG. 3 shows that the cell line was lysed, showing that a model has been developed for screening for a lytic peptide, using a non-human cell.

In experiments not described herein, similar results were obtained with COS cells.

Additional experiments were also carried out, in which cell line P1.HTR A1 was transfected with MAGE-1 cDNA. When the lytic assay of Example 2 was carried out with this co-transfected cells, it was found that they were also lysed.

EXAMPLE 4

Given the homology of the various genes within the MAGE family, a comparison was carried out to identify similarities amongst the homologous regions of the genes. These regions are shown in FIG. 4. These peptides and the nucleic acid sequences coding for them, are not identical, but show a great deal of homology, especially the identical first and ninth residues.

The foregoing examples show that a nonapeptide derived from MAGE-1 is presented by HLA-A1 molecules, and cells presenting the complex of HLA-A1 and the nonapeptide are recognized and lysed by specific CTL cells. This observation indicates that nonapeptides in accordance with the invention may be used both therapeutically and diagnostically.

In the case of the latter category of use, the nonapeptides may be used, for example, to identify tumors expressing a particular HLA molecule, or cancer cells per se. One contacts a cancer cell containing sample or a tumor cell with a nonapeptide which binds thereto, and combines the material with a CTL sample specific for the complex. If lysis ensues, then the tumor/cancer cell can be typed with respect to the HLA molecule thus expressed.

Therapeutically, there are two major ways in which the nonapeptide may be used. In an in vivo therapeutic approach, the nonapeptides may be administered in a way which targets them to tumors to be treated. This can be done via direct injection, time release administration, coupling to tumor specific antibodies, and so forth. Upon binding the requisite HLA molecule, there is a CTL response, leading to lysis of the tumor. Of course, in such a therapeutic approach, the nonapeptide is administered in an amount sufficient to lead to lysis of the tumor. This amount will vary, based upon the particular patient, the type and size of the tumor, and so forth.

An "in vitro" form of therapy is also contemplated. As indicated supra, when the pertinent HLA molecule binds to a MAGE nonapeptide, if contacted with the CTLs specific for the peptide/HLA complex, a CTL proliferative response occurs. As the CTLs are the agents of tumor lysis in vivo, the resulting expanded populations may be administered to the patient. The CTLs can be expanded by using the patient's own blood or any other source of CTLs, or by contact to samples of peptide specific CTLs which have previously been established. In this regard, note that CTL 82/30, discussed supra had been available for some time as was the methodology for its development.

Therapies of the type described herein are particularly useful for melanoma. Analysis of samples has shown that about 40% of all melanoma tumors express MAGE-1. and the HLA-A1 allele is present in about 26% of the Caucasian population at large. Thus, at the least, 10% of the Caucasian melanoma population may be treated in this fashion. The patients may also be treated with non-proliferative cells which have complexes of HLA-A1 and the Mage-1 antigen presented on their surface.

The MAGE-1 derived nonapeptide appears to be HLA-A1 specific. Although the MAGE-2. MAGE-3 and MAGE-4 genes have all been observed to be expressed in HLA-A1 cells of tumors, the peptides corresponding to MAGE-1 have not been shown to elicit the same specific CTL response; however it may be expected that these nonapeptides do provoke response by different CTLs when bound to an appropriate HLA molecule.

The nucleic acid molecules, as indicated, may be used in a variety of ways. MAGE genes are expressed in tumors, and thus the nucleic acid molecules may be used a probes to identify tumor cells. This can be accomplished via labelled hybridization probes, PCR, or any of the various nucleic acid probe based assays known to the art.

The development of the non-human cell lines described herein presents a unique way to carry out some of the features of the invention described herein. The examples show, e.g., that the CTLs recognize the complex of HLA and nonapeptide, and do not appear to differentiate between the cell types which present the complexes. Thus, the isolated, non-human cell lines of the invention can be used to generate CTLs, and to identify their presence in human samples.

As indicated, the invention also involves isolated non-human cell lines transfected with both an HLA gene, and a sequence coding for a nonapeptide, such as HLA-A1 and MAGE-1 nonapeptide. One is not limited to transfection with one HLA coding gene and one MAGE peptide, and indeed the invention contemplates polytransfected cells, which may contain more than one HLA gene and more than one MAGE antigen coding sequence. Such cells may be regarded as universal effector cells, as the presence of appropriate pairs of HLA and peptide on the surface will lead either to identification of specific CTLs of choice, or to generation of CTL proliferation in a therapeutic context. Such cells, be they cotransfected or polytransfected, may serve as vaccines when combined with a suitable adjuvant, such as those well known to the art. Treatment of various cancerous conditions, such as melanoma and breast cancer, may be carried out using these transfectant.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claimed:

1. A method for treating a patient afflicted with a tumor, neoplasm or cancer which expresses a tumor rejection antigen precursor and presents HLA-A1 molecules on cell surfaces of said tumor, neoplasm or cancer, comprising administering to said patient an amount of a nonapeptide, the amino acid sequence of which is set forth at SEQ ID NO: 17, sufficient to form complexes between said nonapeptide and said HLA-A1 molecules and induce lysis of cells of said tumor, neoplasm, or cancer which present complexes of said nonapeptide and said HLA-A1 molecule by cytolytic T cells of said patient.

2. The method of claim 1, wherein said patient expresses tumor rejection antigen precursor MAGE-3.

3. The method of claim 1, wherein said nonapeptide is administered via direct injection, time release administration, or via coupling to a tumor specific antibody.

4. The method of claim 1, wherein said cancer is melanoma.

* * * * *